United States Patent
Lee (10) Patent No.: US 8,354,307 B2
(45) Date of Patent: Jan. 15, 2013

(54) METHOD FOR DETECTING BIOMOLECULES ELECTRICALLY AND BIOCHIP THEREFOR

(75) Inventor: Jae-Hoon Lee, Seoul (KR)

(73) Assignee: Digital Genomics Inc., Seoul (KR)

( * ) Notice: Subject to any disclaimer, the term of this patent is extended or adjusted under 35 U.S.C. 154(b) by 0 days.

(21) Appl. No.: 12/922,934

(22) PCT Filed: Jan. 20, 2009

(86) PCT No.: PCT/KR2009/000285
§ 371 (c)(1),
(2), (4) Date: Sep. 16, 2010

(87) PCT Pub. No.: WO2009/119971
PCT Pub. Date: Oct. 1, 2009

(65) Prior Publication Data
US 2011/0024309 A1    Feb. 3, 2011

(30) Foreign Application Priority Data
Mar. 24, 2008  (KR) ..................... 10-2008-0027099

(51) Int. Cl.
*G01N 15/06*  (2006.01)
*G01N 33/00*  (2006.01)
*G01N 33/48*  (2006.01)
(52) U.S. Cl. ...... 438/149; 422/50; 422/68.1; 422/82.01; 422/82.02; 436/43; 436/63
(58) Field of Classification Search ............ 422/50, 422/68.1, 82.01, 82.02; 436/43, 63, 149
See application file for complete search history.

(56) References Cited

U.S. PATENT DOCUMENTS
7,135,294 B2    11/2006  Lee et al.
(Continued)

FOREIGN PATENT DOCUMENTS
KR    10-2003-0038084 A    5/2003
(Continued)

OTHER PUBLICATIONS

Zou et al.: "Functionalized nano interdigitated electrodes arrays on polymer with integrated microfluidics for direct bio-affinity sensing using impedimetric measurement", Sensors and Actuators A vol. 136 (2007) pp. 518-526 (Published on May 6, 2007).

(Continued)

*Primary Examiner* — Brian J Sines
(74) *Attorney, Agent, or Firm* — Lucas & Mercanti, LLP (57) ABSTRACT

The present invention relates to a method for detecting the presence and/or the reaction of a biomolecule by monitoring changes of electrical property accurately according to the biological, biochemical or chemical reaction of the biomolecule, and a biochip provided for this purpose. The present invention provides a method for detecting the presence and/or the reaction of a biomolecule in a target sample, wherein the reaction of the target sample is performed under known reaction solution, in which a reference fluid having a high dielectric constant such as water is filled into a reaction chamber before the reaction to measure an impedance value or a capacitance value, after completing the reaction, the reaction solution is removed and said reference fluid having a high dielectric constant is refilled to measure an impedance value or a capacitance value, and then the impedance value or the capacitance value measured before and after the reaction is compared with each other.

9 Claims, 6 Drawing Sheets

U.S. PATENT DOCUMENTS

| | | | |
|---|---|---|---|
| 7,857,959 B2 * | 12/2010 | Fourkas et al. | 205/118 |
| 2004/0110277 A1 | 6/2004 | Maeda | |
| 2005/0059105 A1 | 3/2005 | Alocilja et al. | |
| 2006/0226030 A1 | 10/2006 | Hanke et al. | |

FOREIGN PATENT DOCUMENTS

| | | |
|---|---|---|
| KR | 10-2004-0042021 A | 5/2004 |
| KR | 10-2006-0044681 A1 | 5/2006 |
| WO | 2002/055198 A2 | 7/2002 |
| WO | 2008/016703 A1 | 2/2008 |

OTHER PUBLICATIONS

Malave et al.: "Development of impedance biosensors with nanometer gaps for marker-free analytical measurements", Microelectronic Engineering vol. 78-79 (2005) pp. 587-592 (Published on Mar. 1, 2005).

Yi et al.: "Theoretical and experimental study towards a nanogap dielectric biosensor", Biosensors and Bioelectronics vol. 20, No. 7 (2005) pp. 1320-1326 (Published on Jan. 15, 2005).

European Patent Office, "Extended European Search Report", Apr. 8, 2011.

* cited by examiner

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: DNA hybridization chip probe
<220> FEATURE:
<221> NAME/KEY: misc_feature
<222> LOCATION: (1)..(1)
<223> OTHER INFORMATION: A thiol group is attached to a carbon chain
      (-CH2-) at the 5'terminus of the probe oligonucleotide

<400> SEQUENCE: 1
gccattctca ccggattcag tcgtc                                           25

<210> SEQ ID NO 2
<211> LENGTH: 24
<212> TYPE: DNA
<213> ORGANISM: Artificial Sequence
<220> FEATURE:
<223> OTHER INFORMATION: target nucleotide sequence

<400> SEQUENCE: 2
gacgactgaa tccggtgaga atgg                                            24

<210> SEQ ID NO 3
<211> LENGTH: 25
<212> TYPE: DNA
<213> ORGANISM: Artificial Sequence
<220> FEATURE:
<223> OTHER INFORMATION: upstream primer
<220> FEATURE:
<221> NAME/KEY: misc_feature
<222> LOCATION: (1)..(1)
<223> OTHER INFORMATION: A thiol group is attached to a carbon chain
      (-CH2-) at the 5'terminus of the primer oligonucleotide

```
<400> SEQUENCE: 3
gccattctca ccggattcag tcgtc                                      25

<210> SEQ ID NO 4
<211> LENGTH: 22
<212> TYPE: DNA
<213> ORGANISM: Artificial Sequence
<220> FEATURE:
<223> OTHER INFORMATION: downstream primer
<220> FEATURE:
<221> NAME/KEY: misc_feature
<222> LOCATION: (1)..(1)
<223> OTHER INFORMATION: A thiol group is attached to a carbon chain
      (-CH2-) at the 5'terminus of the primer oligonucleotide

<400> SEQUENCE: 4
agccgccgtc ccgtcaagtc ag                                         22
```

METHOD FOR DETECTING BIOMOLECULES ELECTRICALLY AND BIOCHIP THEREFOR

CROSS-REFERENCE TO RELATED APPLICATIONS

This application is a 371 of PCT/KR2009/000285 filed on Jan. 20, 2009, which claims the benefit of Korean Application No. 10-2008-0027099 filed on Mar. 24, 2008, the contents of each of which are incorporated herein by reference.

TECHNICAL FIELD

The present invention relates to a method for detecting the presence and/or the reaction of a biomolecule by monitoring changes of electrical property accurately, after the biological, biochemical or chemical reaction of the biomolecule and a biochip provided therefor.

Particularly, the present invention relates to a method for detecting changes of electrical property, especially the changes of an impedance or capacitance value in a reaction chamber sensitively after the biological, biochemical or chemical reaction of the biomolecule, by using a sensing electrode installed in the reaction chamber and a biochip provided for this purpose.

More particularly, the present invention relates to a method for detecting changes of electrical property such as changes of an impedance or capacitance value sensitively, after a receptor immobilized onto a sensing electrode of a reaction chamber reacts with a biomolecule as a targeting molecule and a biochip used for this purpose.

BACKGROUND ART

Biochip is a device that can analyze genetic information and protein information automatically in a large scale, or detect the presence and the function of a biomolecule easily and rapidly. This biochip is being actively applied for various fields including gene and protein researches, medicines, and agricultural, environmental and chemical industries, etc.

The biochip is classified broadly to genotyping chip, expression chip and microfluidics chip: the genotyping DNA chip is to detect the presence of a particular gene by using a probe; the expression DNA chip is to monitor the expression profiling of gene associated with a particular disease; and the microfluidics chip is to detect the presence and/or the reaction of a biomolecule within a sample including blood and urine. Presently, the genotyping DNA chip is commercialized and used widely in research areas and medical diagnosis areas.

Generally, the term microarray chip defines a chip that arrays hundreds to ten thousands kinds of genes or proteins mounting on a glass plate by using a microarray apparatus. Among these, DNA chip is to microarray oligonucleotides as probes on a glass plate in order to identify the presence of a particular gene with a fluorescence scanner.

The DNA chip is being utilized practically for research and diagnosis fields. Particularly, this chip is applied to elucidate the gene function including cellular metabolism, physiological phenomena and mutual relation between genes by using gene expression profiling and genotyping techniques, etc. The DNA chip is also used widely in diagnosis to examine a mechanism causing a particular disease such as cancer, prognostic diagnosis and action of drugs, to identify genetic information of microbes causing diseases, and to screen mutations, etc.

Diagnostic DNA chip has been developed in 1994 by Dr. Steve Fodor in Affymetrix Co. Ltd., and the first HIV gene chip started to be commercialized in a market. Nowadays, researches upon the diagnostic DNA chip are attempted actively in order to diagnose chronic diseases including HIV, rheumatism, autoimmune disease, chronic nephritis, atherosclerosis, atopic dermatitis and allergy, etc. Especially, recent studies upon DNA chips tend to develop chips for diagnostic use rather than chips for research use. Moreover contrasting to genotyping chips useful for diagnosing genotype, pathogen and virus, an approach on gene expression profiling capable of diagnosing various diseases including cancer and leukemia, is being accomplished.

Recently, microfluidics chip (Lab-on-a chip) that can detect a lot of diseases coincidentally from one trial and predict outbreak of diseases from genetic information of an individual by introducing IT and nano technologies, attracts attention. The microfluidics chip is also referred to as biochip. This chip is used to analyze a reaction profiling of various biomolecules within a chip, after a minute amount of an analytic target material (DNA, RNA, peptide, protein, etc.) is introduced into a chip chamber. This biochip is to detect the presence and/or the reaction of a biomolecule by monitoring changes of electrical property from an electrode installed in a chip, after being reacted with the biomolecule in a reaction chamber.

Such a biochip is highly applicable for medical diagnosis, because it can identify the presence and/or the reaction of a biomolecule more easily and rapidly by detecting electrical signals than any other DNA chips mentioned above.

For example, HPV DNA chip is a device that prepares HPV oligonucleotide probes and microarrays these probes on a glass plate in order to diagnose whether HPV, a pathogenic virus causing cervical cancer is positive or not. Nevertheless, it is impossible to directly diagnose the positive status of HPV, right after suspected sample is collected. That is to say, primers for amplifying HPV viral gene, labeled with fluorescence should be prepared in advance. Then, the collected sample should be amplified by performing a PCR, mounted onto an HPV DNA chip and monitored to examine a fluorescent signal with a fluorescence scanner. However, this system for detecting hybrids by using a DNA chip (laser-induced fluorescence) is inconvenient to be manipulated and spends time a lot. Therefore, this method has various problems and disadvantages. It needs high cost due to labeling a DNA sample with a fluorescent material and is not portable because of using an expensive fluorescence scanner.

In contrast, the biochip can identify the presence and/or the reaction of a biomolecule relatively easily and rapidly by detecting electrical signals. Particularly, the biochip can detect the presence and/or the reaction of a biomolecule (for example, DNA) by using electrical signals rather than fluorescent signals. More particularly, the biochip adopts a system for detecting changes electrically, in which the change of an impedance value (or a capacitance value) is monitored after reacting a receptor immobilized onto an electrode with a biomolecule, or the change of an impedance value (or a capacitance value) is monitored after reacting between biomolecules in a chip chamber.

For example, it is reported in the PCR process that dNTP should degrade to dNMP and diphosphate and the resulting dNMP is polymerized simultaneously from a primer complementary to a DNA template sequence so as to synthesize DNA. Accordingly, the impedance value within a PCR reagent increases as DNA concentration increases (See Korean Patent Laid-open NO. 10-2004-0042021). Therefore, it is possible to determine whether the PCR reaction is performed and a particular DNA sequence exists or not, when a PCR reaction chamber is manufactured with a biochip structure and the changes of an impedance value in a reagent are detected electrically on an electrode installed in such a biochip.

In addition, it is possible to detect electrically whether a PCR reaction or a hybridization reaction is accomplished and/or whether a target nucleotide sequence exists or not, when oligonucleotides such as primers or probes are immobilized on a biochip electrode, a PCR reaction or a hybridization reaction is conducted and then, the changes of a capacitance or impedance value are measured with the electrode on which the oligonucleotides are immobilized.

In general, the biochip adopts a system for determining the reaction and the presence of a particular biomolecule by monitoring the impedance change with an electrode equipped in the biochip after reacting the biomolecule and other reagents (for example, the receptor immobilized onto an electrode). Accordingly in order to guarantee the reliability of a biochip, it is important to measure the change of the impedance value accurately. Generally, impedance (Z) indicates the sum of resistance (R) as a real number portion and reactance (X) as an imaginary number portion (See following Mathematical formula 1), and the magnitude of impedance corresponds to a square root of resistance score (R) and reactance score (X) (See following Mathematical formula 2).

$$Z = R + jX$$
$$= R + j(X_L - X_C)$$
$$= R + j\left(\omega L - \frac{1}{\omega C}\right) [\Omega]$$

[Mathematical formula 1]

$$|Z| = \sqrt{R^2 + X^2}$$
$$= \sqrt{R^2 + \left(\omega L - \frac{1}{\omega C}\right)^2} [\Omega]$$

[Mathematical formula 2]

Accordingly, the impedance (Z) value is made to have a correlation with reactance (X). Also, the reactance (X) has a correlation with the capacitance (C) value because it is $\omega L - 1/\omega C$. Therefore, the change of the capacitance (C) value varying according to biological, biochemical or chemical reactions, is reflected by the change of the impedance value, which enables to check the reaction and/or the presence of a biomolecule after its measurement. Finally, it is verified that the change of the capacitance value should change the impedance value in a biochip and influence upon the sensitivity of the biochip.

The change of the impedance value can be affected by two kinds of capacitance values after reacting the biomolecule and other reagents (for example, the receptor immobilized onto an electrode). Particularly, when the change of the capacitance value is measured by the electrode of a biochip, total change of capacitance value ($C_T$) in a biochip can include change of a capacitance value ($C_d$) on the surface of a sensing electrode after reacting a receptor immobilized onto an electrode with a biomolecule, and a capacitance value ($C_t$) between an imaginary electrode plate and another sensing electrode, which is different from the change of the capacitance value ($C_d$) (See following Mathematical formula 3).

$$C_T = \frac{1}{\frac{1}{C_t} + \frac{1}{C_d}}$$

[Mathematical formula 3]

In a biochip, the biomolecule is reacted under a reagent filling a reaction chamber and the reagent generally contains a buffer solution or electrolytes. The buffer solution and electrolytes contain ions to influence conductance between sensing electrodes of a biochip. This buffer effect upon the conductance between sensing electrodes further affects the capacitance value ($C_t$) between the imaginary electrode plate and another sensing electrode, which are contained in the buffer functioning as a dielectric substance. Finally, this influences total change of the capacitance value ($C_T$).

On the other hand, the capacitance value depends on the dielectric constant of a material between electrodes as defined in following Mathematical formula 4. It is verified that when the dielectric constant of a material between electrodes is small, the capacitance value becomes small.

$$C = \frac{Q}{V} = \varepsilon \frac{A}{t}$$

[Mathematical formula 4]

A: area of electrode

T: interval between electrodes

ε: dielectric constant of material between electrodes

However, the reagent such as the above-mentioned buffer has a small dielectric constant due to the ion conductivity and thus, $1/C_t$, an element comprising total change of the capacitance value ($C_T$) becomes large in Mathematical formula 3. Accordingly, when the biomolecule is reacted under a buffer solution filled in the reaction chamber of a biochip, the capacitance value ($C_d$) changed by the reaction between the sensing electrode and the biomolecule can be absorbed into the capacitance value ($C_t$) between the imaginary electrode plate and the another sensing electrode contained in the buffer functioning as a dielectric substance. Particularly as demonstrated in the Mathematical formula 3, the capacitance value ($C_d$) changed on the surface of the sensing electrode by reacting the receptor immobilized onto the electrode with the biomolecule does not influence the total change of the capacitance value ($C_T$), because the reciprocal number ($1/C_t$) of the capacitance value ($C_t$) between the imaginary electrode plate and the another sensing electrode filled with the reagent containing buffer ions as a dielectric substance is large. Therefore, it is difficult problematically to determine the presence and/or the reaction of a biomolecule by the electrical detection using the sensing electrode of a biochip.

Figure 1:
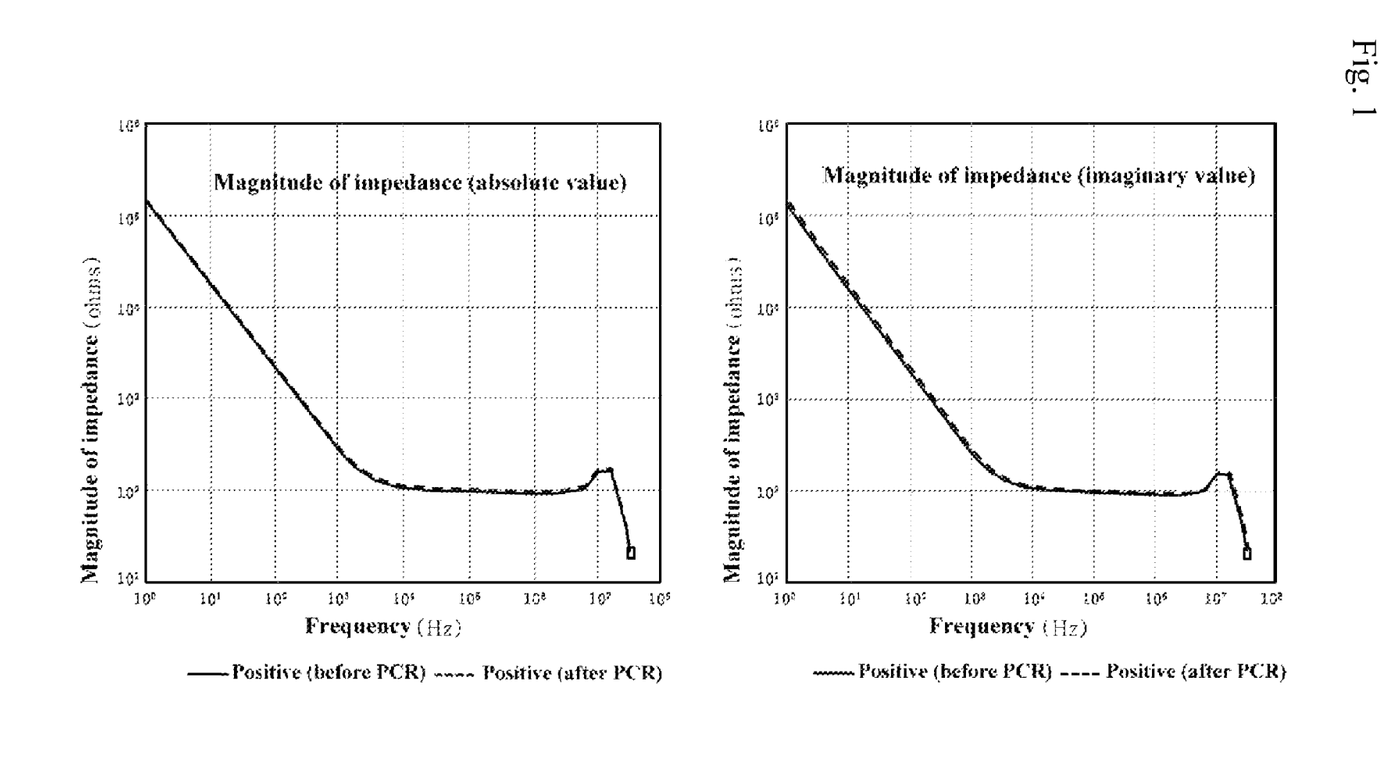
FIG. 1 depicts the change of the impedance value measured by using a conventional system for detecting a PCR reaction.

Referring to this, FIG. 1 illustrates that the curve of the impedance value varied according to frequency is observed to have the same trend before and after PCR reaction, even though a particular target DNA template as a diagnostic sample exists. If conventional biochip could measure PCR reaction using a particular target DNA template as a biomolecule accurately, the change of the capacitance value ($C_d$) on the surface of a sensing electrode could be detected electrically after the PCR reaction between a primer fixed onto the sensing electrode and a template ssDNA. The change pattern of impedance curves might also be observed before and after the PCR reaction, because the change of the capacitance value ($C_d$) on the surface of the sensing electrode should be reflected after DNA amplification by the PCR reaction.

However, since the capacitance value ($C_d$) changed after reacting a sensing electrode and a biomolecule may be passed over by the capacitance value ($C_t$) between an imaginary electrode plate and another sensing electrode as described above, the impedance curve is not changed and just observed as a single curve before and after the PCR reaction, when being measured with an biochip-connected apparatus monitoring an impedance value (See FIG. 1). Therefore, in biochips of prior arts, the capacitance value ($C_d$) changed by reacting a receptor immobilized onto an electrode and a biomolecule, is passed over by the capacitance value ($C_t$) between an imaginary electrode plate and another sensing electrode containing a buffer solution as a dielectric substance, and thus, two curves of the changes of the impedance value which mean total change of the capacitance value ($C_T$)

are not measured. Problematically, it is difficult to monitor whether the biomolecule reacts and/or exists or not in practice.

Particularly, in US Patent Laid-open No. 2004/0110277, the system for sensing a hybridization reaction, in which a probe DNA is immobilized onto an electrode of sensor cell in a biosensor and hybridized with a target DNA to change a capacitance value and finally, a current value of a transistor, has been disclosed. However, it does not focus to settle following problem: since the capacitance value ($C_d$) changed by reacting a receptor immobilized onto an electrode with a biomolecule is passed over by the capacitance value ($C_t$) of the buffer solution, the reaction between the receptor immobilized onto the electrode and the biomolecule as a target material cannot be detected electrically.

Besides, in US Patent Laid-open NO. 2006/0226030, the technique for sensing a hybridization reaction by detecting a capacitance value with a sensor comprising a plate, an electrode and a catcher molecule immobilized on the plate, in which the catcher molecule is hybridized with DNA single strand labeled with metallic ball (having a different dielectric constant from that of the other material) and as a result, the label surrounds the electrode to change a part of the capacitance value regarding an electrode impedance value, has been disclosed. However, it did not pay attention to overcome following problem: since the capacitance value ($C_d$) changed by reacting a receptor immobilized onto an electrode with a biomolecule is passed over by the capacitance value ($C_t$) of a buffer solution, changes of electrical property can not be detected sensitively during actual reaction.

Furthermore, in conventional techniques, a system for increasing sensing sensitivity of IDE by reducing the interval of sensor electrodes in order to improve the sensing sensitivity of a biochip, has been disclosed. But, it did not recognize the problem mentioned above: since the capacitance value ($C_d$) changed by actual reaction is passed over by the capacitance value ($C_t$) of a buffer solution, the changes of the capacitance value and the impedance value cannot be detected sensitively.

Therefore, conventional biochips and methods using the same for identifying the reaction and/or the presence of biomolecules disclosed in prior arts should be improved.

In order to settle above-mentioned problems, the present inventors have accomplished to design a method for detecting a biomolecule and a biochip therefor, wherein the dielectric constant of a material filled between electrodes within a reaction chamber of a biochip is made large, which does not distort actual change of the capacitance value when reacting on the surface of a sensing electrode, and thus, reflects accurately the biological, biochemical or chemical reaction of a biomolecule in a reaction chamber.

DISCLOSURE

Object

The present invention aims to settle the above-mentioned disadvantage that cannot monitor sensitively a capacitance value changed in an electrode of a biosensor during actual reaction in prior arts. The object of the present invention is to provide a method for detecting the presence and/or the reaction of a biomolecule by accurately monitoring changes of electrical property after biological, biochemical or chemical reaction of a biomolecule in a reaction chamber and a biochip provided therefor.

Particularly, the object of the present invention is to provide a method for detecting changes of electrical property, especially changes of an impedance or capacitance value accurately after biological, biochemical or chemical reaction of a biomolecule in a reaction chamber, by using a sensing electrode installed in the reaction chamber and a biochip provided for this purpose.

More particularly, the object of the present invention is to provide a method for detecting a biomolecule and a biochip used for this purpose, wherein the dielectric constant of a material filled between electrodes within a reaction chamber of a biochip is made large, which does not distort actual changes of a capacitance value when reacting on the surface of a sensing electrode and thus, accurately reflects the biological, biochemical or chemical reaction of a biomolecule in a reaction chamber.

Technical Solution

In order to overcome the above-mentioned disadvantage of conventional methods, it is necessary to discriminate the capacitance value ($C_d$) changed by reacting a receptor immobilized onto an electrode with a biomolecule from the capacitance value ($C_t$) of a buffer solution so that the capacitance value ($C_d$) should not be passed over by the capacitance value ($C_t$). For this purpose, $1/C_t$ score needs to become smaller and namely, $C_t$ score needs to become larger.

Meanwhile, the capacitance value is defined as described in the mathematical formula 4. Accordingly, the area of electrode should become larger, the interval between electrodes should become narrower, or the dielectric constant of a material filled between electrodes should become larger in order to increase $C_t$ score.

In prior arts, the system for increasing sensing sensitivity, in which the width of a sensor electrode is decreased in IDE (interdigitated electrode) of a biochip in order to increase $C_t$, has adopted as described above. However, the decrease of electrode width may not be preferred in respect of cost and efficiency, since it requires a highly advanced microelectrode formation technique.

Considering such a disadvantage, the present invention has attempted a system for increasing dielectric constant ∈(or also referred to as dielectric ratio) of a material filled between electrodes in a reaction chamber of a biochip. This method does not require a highly advanced technique of microelectrode formation, as well as not distort actual changes of a capacitance value when reacting on the surface of a sensing electrode, and can accurately reflect the biological, biochemical or chemical reaction of a biomolecule in a reaction chamber.

In the meantime, the biochip is filled with a reagent for reacting a target sample between electrodes of a reaction chamber. Accordingly, it is required to increase the dielectric constant of this reagent. But, this reagent for reacting a target sample is difficult to modulate the dielectric constant due to ions.

Generally, the dielectric constant is defined as the ratio of the capacity measured when a dielectric substance is filled between electrodes to the capacity measured when nothing is filled between electrodes, and the dielectric ratio of any dielectric substance is always larger than 1. Among liquid, the dielectric constant of water is known to be largest and approximately 80 at room temperature. However, in order to test a target sample, water such as distilled water or deionized water cannot be used for reagent use directly.

Therefore, the present invention provides a method for detecting the presence and/or the reaction of a biomolecule in a target sample, wherein the reaction of the target sample is performed under known reaction solution, in which a reference fluid having a high dielectric constant such as water is filled into a reaction chamber before the reaction to measure an impedance value or a capacitance value, after completing the reaction, the reaction solution is removed and said reference fluid having a high dielectric constant is refilled to measure an impedance value or a capacitance value, and then the impedance value or the capacitance value measured before and after the reaction is compared with each other.

Particularly, the present invention provides a method for detecting a biomolecule electrically, which comprises: (a) providing an apparatus for electrical detection comprising a reaction chamber receiving a target sample, and a plurality of sensing electrodes located in the reaction chamber for detecting a biomolecule within the target sample; (b) measuring an impedance value or a capacitance value between the sensing electrodes, after introducing a reference fluid having a high dielectric constant into the reaction chamber; (c) providing a reaction solution and the target sample into the reaction chamber, after removing the reference fluid having a high dielectric constant from the reaction chamber; (d) reacting the target sample under the reaction solution in the reaction chamber; (e) removing the reaction solution from the reaction chamber; (f) measuring an impedance value or a capacitance value between the sensing electrodes, after introducing said reference fluid having a high dielectric constant again into the reaction chamber; and (g) comparing the impedance value or the capacitance value measured in the step (b) with the impedance value or the capacitance value measured in the step (f).

In an embodiment of the present invention, the impedance value or the capacitance value is measured according to frequency in the step (b) and the step (f), respectively by a measuring device using alternating current (AC) electric source. In this case, the impedance value or the capacitance value measured is illustrated as curves with respect to the frequency value. In case that the curve of the impedance value or the capacitance value obtained in the step (b) is discriminated from the curve of the impedance value or the capacitance value obtained in the step (f), this result is judged to show the presence of the target biomolecule or the reaction of the target biomolecule onto the sensing electrode within the target sample.

In another embodiment of the present invention, the reference fluid having a high dielectric constant is preferable to have approximately more than 4 of dielectric constant, more preferably to have approximately more than 80 of dielectric constant. The reference fluid having a high dielectric constant can be distilled water or deionized water, but the present invention is not limited hereto. Any fluid can be applicable, if it has approximately more than 4 of dielectric constant as described above.

In another embodiment of the present invention, the sensing electrodes are preferably made of gold, chrome, copper or aluminum. Preferably, the sensing electrodes are formed of interdigitated electrode, and each interval between the sensing electrodes can be approximately 1 to 20 μm and preferably, approximately 1 to 4 μm.

In another embodiment of the present invention, a plurality of the sensing electrodes can be bound with a receptor capable of interacting with the biomolecule.

In another embodiment of the present invention, the term "biomolecule" is a material that interacts with the receptor combined on the sensing electrode and can include nucleic acids comprising one or more nucleotides, proteins comprising one or more peptides, amino acids, glycolipids or small molecule compounds, and preferably an antigen, DNA, RNA or PNA (peptide nucleic acid).

In another embodiment of the present invention, the term "receptor" is a material combined on the sensing electrode, which interacts with the biomolecule and can include nucleic acids comprising one or more nucleotides, proteins comprising one or more peptides, amino acids, glycolipids or small molecule compounds, and preferably an antigen, a probe or a primer.

In addition, in another embodiment of the present invention, the receptor has a feature to be an oligonucleotide probe, the biomolecule is the nucleic acid, and the reaction solution is a solution for nucleic acid hybridization. Further, in another embodiment of the present invention, the receptor has a feature to be an oligonucleotide primer, the biomolecule is the nucleic acid, and the reaction solution is a solution for PCR amplification.

In addition, the biochip of the present invention used in the method for detecting a biomolecule can be manufactured in a form of single plate, but can be in a combined form of two plates. In an embodiment of the present invention, this biochip can include a DNA hybridization chip or a PCR reaction chip.

In another embodiment of the present invention, the biochip having a combined form of two plates comprises a first plate that has a plurality of sensing electrodes bound with a receptor interacting with a biomolecule, and a second plate that forms a space of a reaction chamber with respect to the first plate by being combined with the first plate in a predetermined distance.

The first plate has a plurality of sensing electrodes formed on $SiO_2$ insulation layer on N-type or P-type silicon plate, which performs electrical detection in order to identify whether a biomolecule exists and/or reacts or not. The second plate prevents the sensing electrodes of the first plate from contacting outside environment to form a space of a reaction chamber by being combined with the first plate.

The reaction chamber is a space where an impedance value and/or a capacitance value are measured between electrodes after being filled with a reference fluid having a high dielectric constant. In addition, the reaction chamber is a space where a biomolecule in the target sample is reacted after being filled with the reaction solution and the target sample. In case that the receptor is immobilized on the sensing electrode, the biomolecule within the reaction chamber reacts with the receptor and as a result, the changes of an impedance value and/or a capacitance value between electrodes occur.

The above-mentioned plates can have various sizes, depending upon the kind and the number of applicable receptors, for example the kind and the number of probes and primers. In addition, the plates can have square shape, rectangular shape, and circular shape, but are not limited hereto in the present invention. Preferably, the first plate may be a silicon plate, and the second plate may be a glass plate. But, these plates can be also constructed by any one selected from the group consisting of glass, silicon, fused silica, polystylene, polymethylacrylate, polycarbonate, gold, silver, copper and platinum.

In addition, the second plate forming the space of the reaction chamber is perforated to have a fluid inlet in the direction of thickness and further perforated to have a fluid outlet in the direction of thickness on the opposite side of the fluid inlet. The inlet and the reaction chamber, and the outlet and the reaction chamber are communicated with each other to allow fluid to flow therethrough in the reaction chamber. The reference fluid having a high dielectric constant, the reaction solution and the target sample are introduced through the inlet, and the reference fluid having a high dielectric constant, the reaction solution and the target sample flow outside through the outlet.

In addition, an inlet micro channel that directs to introduce fluid into the inlet, and an outlet micro channel that directs to discharge fluid from the outlet can be made by layering a third plate on the second plate. The inlet micro channel is communicated with an injection opening into which the reference fluid having a high dielectric constant, the reaction solution and the target sample are injected, and penetrates through the third plate. The outlet micro channel is communicated with a discharge opening into which the reference fluid having a high dielectric constant, the reaction solution and the target sample are discharged, and penetrates through the third plate.

In addition, a valve structure that can control fluid injection into the space of the reaction chamber and fluid discharge from the space of the reaction chamber can be provided on the inlet micro channel and/or the outlet micro channel. The valve structure is a passage extended after being penetrated into the third plate in the direction of thickness, between the injection opening and the space of the reaction chamber, or between the discharge opening and the space of the reaction chamber wherein oil is stored in said passage. When nitrogen gas ($N_2$) is injected into this passage of the valve structure, the oil stored in the passage expands and blocks the channels due to the oil expansion so as to obstruct inflow of fluid from the injection opening to the reaction chamber and outflow of fluid from the reaction chamber to the discharge opening. Preferably, the third plate is made of PDMS (polydimethylsiloxane).

The micro channel and the valve structure mentioned above can be prepared in a micron unit or nano unit by using a MEMS (micro-electro-mechanical-system) technique used widely in this field, and their size can be controlled, depending upon receptor size, electrode size, or reaction condition.

The channel structure and the valve structure facilitate following steps in the above-mentioned method: filling the reference fluid having a high dielectric constant into the reaction chamber before reaction; removing the reference fluid having a high dielectric constant from the reaction chamber and filling the reaction solution and the target sample into the reaction chamber during reaction; and removing the reaction solution from the reaction chamber and refilling the reference fluid having a high dielectric constant into the reaction chamber after the reaction. For this purpose, the biochip can be provided with an injection pump and a discharge pump in order to inject and remove the fluid, the reaction solution and the target sample. For driving a pump, the biochip can also be provided with a small motor or a gearbox.

On the other hand, an impedance analyzer can be connected electrically to a plurality of sensing electrodes. When this biochip is a PCR reaction chip, a PCR device for conducting PCR reaction can be manufactured to accommodate a biochip and thus, the biochip and the PCR device can be provided as one set. Preferably, when the biochip and the PCR device are provided as one set, the PCR device having an impedance measuring apparatus is used and the impedance measuring apparatus is connected electrically to sensing electrodes of the biochip.

Advantageous Effects

As illustrated and confirmed above, the method of present invention can detect the change of electrical property accurately according to biological, biochemical or chemical reactions of the biomolecule within the reaction chamber, even though the capacitance value ($C_d$) changed on the surface of sensing electrodes may be passed over by the capacitance value ($C_t$) of the buffer solution.

Particularly, the present invention is advantageous to make the dielectric constant of a material filled between electrodes within the reaction chamber of the biochip large, which does not distort actual change of a capacitance value when reacting the biomolecule in the target sample with the receptors immobilized on the surface of sensing electrodes, and can reflect total change of the capacitance value accurately and thus, detect the presence and/or the reaction of the biomolecule sensitively.

BRIEF DESCRIPTION OF DRAWINGS

The above and other objects, features and other advantages of the present invention will be more clearly understood from the following detailed description taken in conjunction with the accompanying drawings, in which;

FIG. 3 (a) shows the whole electrode portion of the DNA hybridization chip, FIG. 3 (b) depicts schematically a magnified part of the electrode of FIG. 3 (a), and FIG. 3 (c) depicts a pair of electrodes (20a, 20b) having a finger shape which are partially magnified.

FIG. 5 (A) illustrates a process for preparing a silicon plate of a PCR reaction chip, FIG. 5 (B) illustrates a process for preparing a glass plate of a PCR reaction chip, and FIG. 5 (C) depicts the binding state of the silicon plate and the glass plate.

FIG. 6. (A) depicts a fluid controlling plate attached on the glass plate of the PCR reaction chip manufactured previously. FIG. 6. (B) and (C) illustrate a procedure for controlling fluid flow in the PCR reaction chip by a valve function of the fluid controlling plate.

MODE FOR INVENTION

Practical and presently preferred embodiments of the present invention are illustrated more clearly as shown in the following examples.

However, it should be appreciated that those skilled in the art, on consideration of this disclosure, may make modifications and improvements within the spirit and scope of the present invention. References cited in the specification are incorporated into the present invention.

EXAMPLES

Example 1

Preparation of a DNA Hybridization Chip

In the method for detecting a biomolecule of the present invention, when a target biomolecule is DNA and a receptor combining with a sensing electrode is an oligonucleotide probe, a DNA hybridization chip for hybridizing a probe and DNA as a biomolecule is prepared.

The DNA hybridization chip sensor is manufactured by using a general procedure disclosed in this field, including thin film formation technique of silicon dioxide, photolithography technique, exposure patterning technique, developing technique, wet and/or dry etching technique, etc. Particularly, sensing metal electrodes having an IDE (interdigitated electrode) are formed on a silicon plate by using a MEMS (micro-electro-mechanical-systems) and then, oligonucleotide probes are immobilized on the sensing electrodes.

The process for preparing the DNA hybridization chip used in the present invention will be described according to stages as follows.

Example 1-1

Construction of a Silicon Plate on which Electrodes are Formed

Hereinafter, referring to FIG. 2, the procedure for forming a plate (10) and an electrode (20) of the DNA hybridization chip (100) used in the present invention will be explained briefly.

Figure 2:
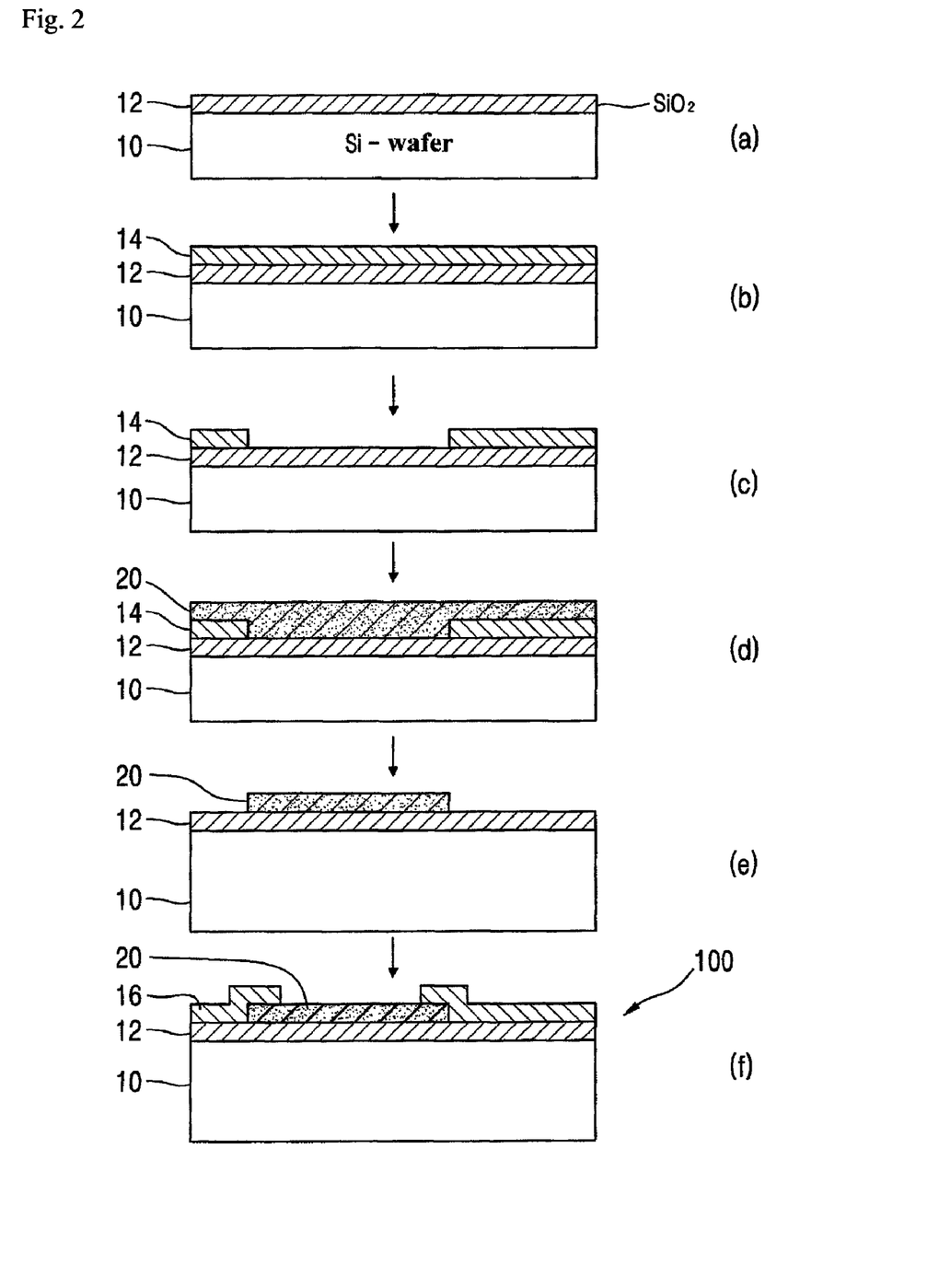
FIG. 2 is a flow chart of process that illustrates a method for preparing a DNA hybridization chip used in the present invention.

N-type silicon wafer (10) having 500 µm of thickness was thermally oxidized to make about 10,000 Å of a $SiO_2$ layer (12), an oxidized insulation layer (See the Step (a) of FIG. 2). Then, the insulation layer (12) was coated with a photoresist AZ 5214 (14) (See the Step (b) of FIG. 2). On the photoresist (14), a mask having a pattern of metal electrodes (not shown) was mounted and exposed with ultra violet light. After that, the silicon wafer (10) was immersed in AZ300MIF developing solution to be developed and etch-treated (See the Step (c) of FIG. 2). On the etched wafer (10), a thin film (20) of chrome (Cr) (300 Å) and gold (Au) (3000 Å) was deposited (See the Step (d) of FIG. 2). The deposition of the thin film (20) of chrome and gold was performed by using chemical vapor deposition (CVD), vacuum evaporation or sputtering. Then, the photoresist layer (14) remained and a part of the thin film on the photoresist layer (14) remained were removed by using a known lift-off process so as to make a metal electrode (20) (See the Step (e) of FIG. 2). In order to form a metal electrode in the format of an IDE (interdigitated electrode), a photoresist AZ4620 (16) was additionally coated and the electrode (20) was patterned to form a fine IDE by using a known photolithography procedure in this field (See the Step (f) of FIG. 2).

Figure 3:
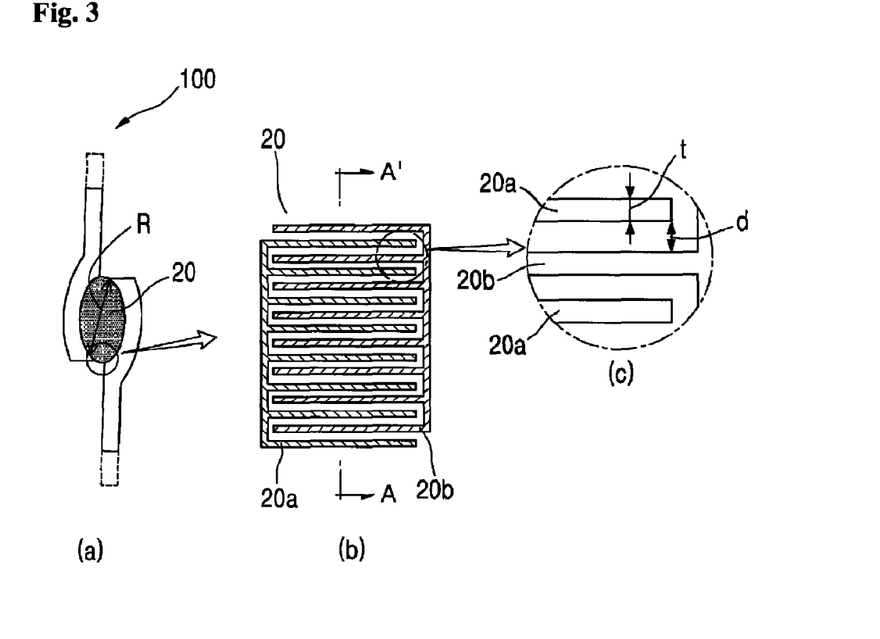
FIG. 3 is a top plane view illustrating the electrode portion of the DNA hybridization chip manufactured according to the process of FIG. 2.

The DNA hybridization chip (100) manufactured is illustrated in FIG. 3. The DNA hybridization chip (100) depicted in FIG. 3 (a) has approximately 2.4 mm of diameter (R) in the electrode (20), but is better to have as small diameter as possible in order to manufacture an electrode array type DNA hybridization chip (See FIG. 7). The area of the electrode (20) is approximately 3.6 $mm^2$.

In FIG. 3 (b), the electrode depicted in FIG. 3 (a) is magnified partially and illustrated schematically. In order to be understood easily, the shape of the electrode (20) is illustrated with a rectangle, but an actual electrode (20) may be round or elliptic. As illustrated in FIG. 3 (b), it is confirmed that the sensing electrodes (20) of the DNA hybridization chip (100) used in the present invention have a pair of electrodes (20a, 20b) wherein they are arrayed alternately in a predetermined interval with a finger-like shape.

On the other hand, the pair of electrodes (20a, 20b) having a finger-like shape is magnified partially as illustrated in FIG. 3 (c). The width (t) of each electrode (20a, 20b) is approximately 10 µm and the interval (d) between the electrodes is approximately 4 µm.

Example 1-2

Immobilization of Oligonucleotide Probes on an Electrode

Above all, the electrodes (20) of the DNA hybridization chip (100) prepared in Example 1-1 were washed with oxygen plasma (150 W, 100 mtorr) for 10 seconds in order to remove impurities on the electrodes (20) completely. Then, one end of a probe DNA (5' or 3') was immobilized on the electrode (20). For this immobilization, a probe 5'-SH—$(CH_2)_{24}$-GCC ATT CTC ACC GGA TTC AGT CGT C-3', in which a thiol group is attached to a carbon chain (—$CH_2$—) at the 5' terminus of the probe oligonucleotide, is prepared and fixed on the surface of the metal electrode (20) by using a SAM (self-assembled method). In detail, 10 pmol/µl of SH-ssDNA probe was reacted under $MgCl_2$ solution condition for 18 hours. As a result, —SH group of the probe reacts on the metal surface to immobilize the probe DNA (22) on the surface of the metal electrode (20) (See FIG. 4).

Meanwhile, a conductive polymer can be bound to a probe DNA instead of a thiol group, and the conductive polymer bound to DNA can be immobilized onto the surface of the metal electrode by using a SAM method (self assembled method). All the conductive polymers known in this field, for example, especially high-conductive polymer including polyacetylene, poly(p-phenylene) (PPP), polypyrrole (PPy), polyaniline, polythiophene, etc. may be used. The conductive polymer can be bound to the probe DNA by using a known binding method regarding binding between a polymer and DNA.

Figure 4:
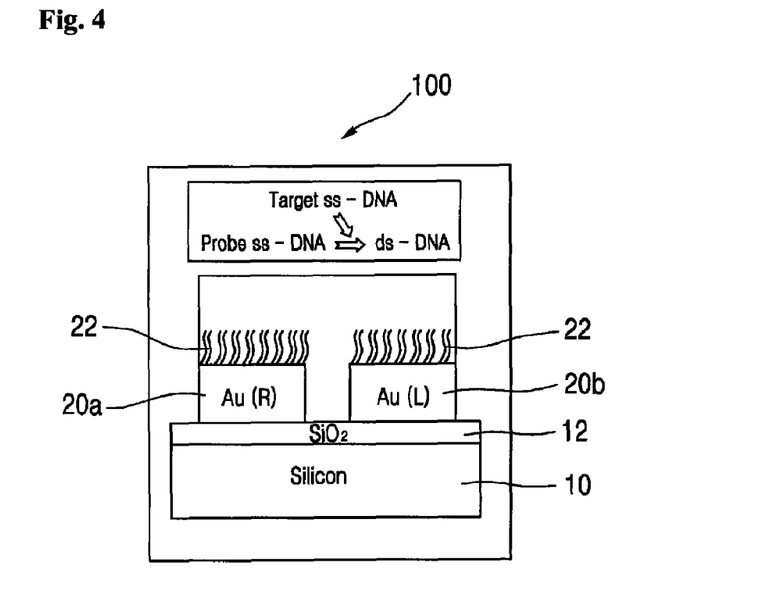
FIG. 4 is a cross sectional view of the metal electrode (20) of FIG. 3 (b) sectioned according to A-A' line.

FIG. 4 is a cross sectional view of the metal electrode (20) of FIG. 3 (b) sectioned according to A-A' line and illustrates the immobilization of the DNA probes (22) on the metal electrodes (20a, 20b) formed on the silicon plate wherein the oxidized insulation layer (12) intervenes between the metal electrodes (20a, 20b) and the silicon plate (10).

Example 2

Detection of a Target Nucleotide Sequence Using the DNA Hybridization Chip

The DNA hybridization chip (100) of FIG. 4 manufactured in Example 1-2 was used to examine whether a target nucleotide sequence (5'-GAC GAC TGA ATC CGG TGA GAA TGG-3') is found within a target sample or not.

Above all, deionized water as a reference solution having a high dielectric constant was introduced into a reaction space between electrodes (20) of the DNA hybridization chip (100) and then, the impedance value between the electrodes (20) was measured at room temperature by applying AC power. The applied magnitude of AC power was 100 mV and its frequency range was 1 to 32 MHz when the impedance value was measured.

After that, the reference solution was removed from the DNA hybridization chip (100) and then, the target sample containing the target nucleotide sequence (10 pmol/µl of ssDNA) and TE buffer were introduced into the reaction space of the DNA hybridization chip (100). The resultant was incubated for 18 hours at room temperature depending upon hybridization condition to hybridize the probe DNA (22) immobilized onto the electrode (20) of the DNA hybridization chip (100) with ssDNA of the target nucleotide sequence (5'-GAC GAC TGA ATC CGG TGA GAA TGG-3').

Again, the buffer solution was removed from the DNA hybridization chip (100) and deionized water was introduced. Then, the impedance value between the electrodes (20) was measured at room temperature by applying AC power. The applied magnitude of AC power was 100 mV and its frequency range was 1 to 32 MHz when the impedance value was measured.

Figure 8:
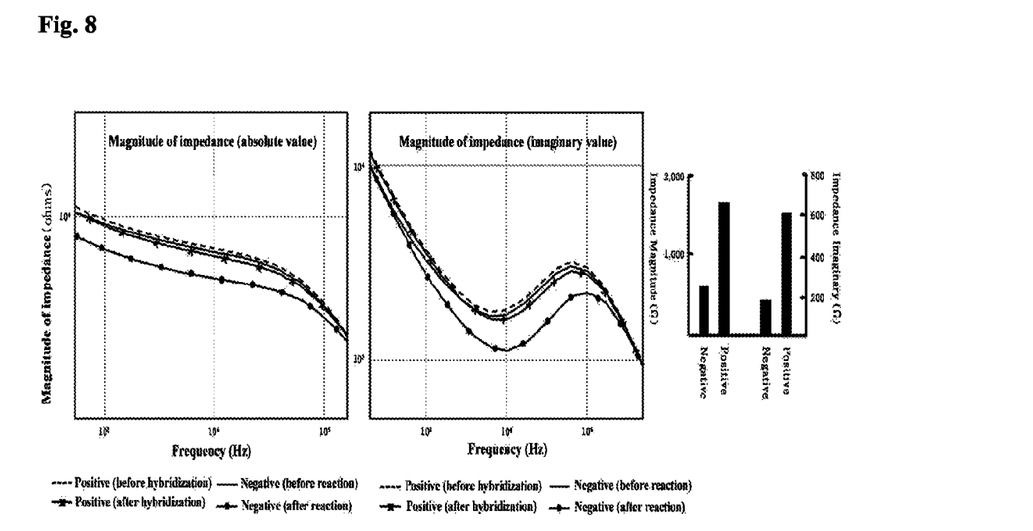
FIG. 8 depicts the change curve of the impedance value measured by using the method for detecting DNA hybridization reaction in the present invention.

As described above, the impedance value measured before the hybridization reaction and the impedance value measured after the hybridization reaction are illustrated in FIG. 8. In FIG. 8, contrasting to FIG. 1 in case of a conventional method, the impedance value measured before the hybridization reaction and the impedance value measured after the hybridization reaction were observed with two different curves, when this experiment is conducted by using a positive target sample containing the target nucleotide sequence. As illustrated in FIG. 8, it is confirmed that the impedance value should decrease when the target DNA exists in the reaction solution during the hybridization reaction. Therefore, it is confirmed that the impedance value will decrease as the conductance value increases due to the hybridization from ss-DNA to ds-DNA during the hybridization reaction.

In the method of the present invention, the change of the capacitance value ($C_d$) after hybridizing a target ssDNA with a probe immobilized on a sensing electrode should reflect total change of the capacitance value ($C_T$) since it is not passed over by the capacitance value ($C_t$) of a buffer solution. Hence, the method of the present invention can permit electrical monitoring to detect the hybridization reaction and the presence of target DNA, because two curves of the changes of the impedance value are observed before and after the hybridization as shown in FIG. 8.

On the other hand, it is observed that the impedance value measured from a negative target sample without a target nucleotide sequence should be smaller than the impedance value of the positive case as shown in FIG. 8.

Example 3

Construction of a PCR Reaction Chip

In the method for detecting a biomolecule of the present invention, when a target biomolecule is DNA and a receptor combining with a sensing electrode is an oligonucleotide primer, a PCR reaction chip for amplifying DNA as a target biomolecule by using a primer and a PCR reagent is manufactured.

Like the DNA hybridization chip sensor, the PCR reaction chip is also manufactured by using a general procedure disclosed in this field. A silicon plate and an electrode portion can be manufactured by using thin film formation technique of silicon dioxide, photolithography technique, exposure patterning technique, developing technique, wet and/or dry etching technique, etc. The sensing metal electrodes having an IDE (interdigitated electrode) are formed on the silicon plate by using a MEMS (micro-electro-mechanical-systems) and then, the oligonucleotide primers are immobilized on the sensing electrodes. In addition, a glass plate attached to the silicon plate is made by using glass wet etching and sand blasting technique.

The process for preparing the PCR reaction chip used in the present invention will be described according to stages as follows.

Example 3-1

Construction of a Silicon Plate, Electrodes and a Glass Plate

Figure 5:
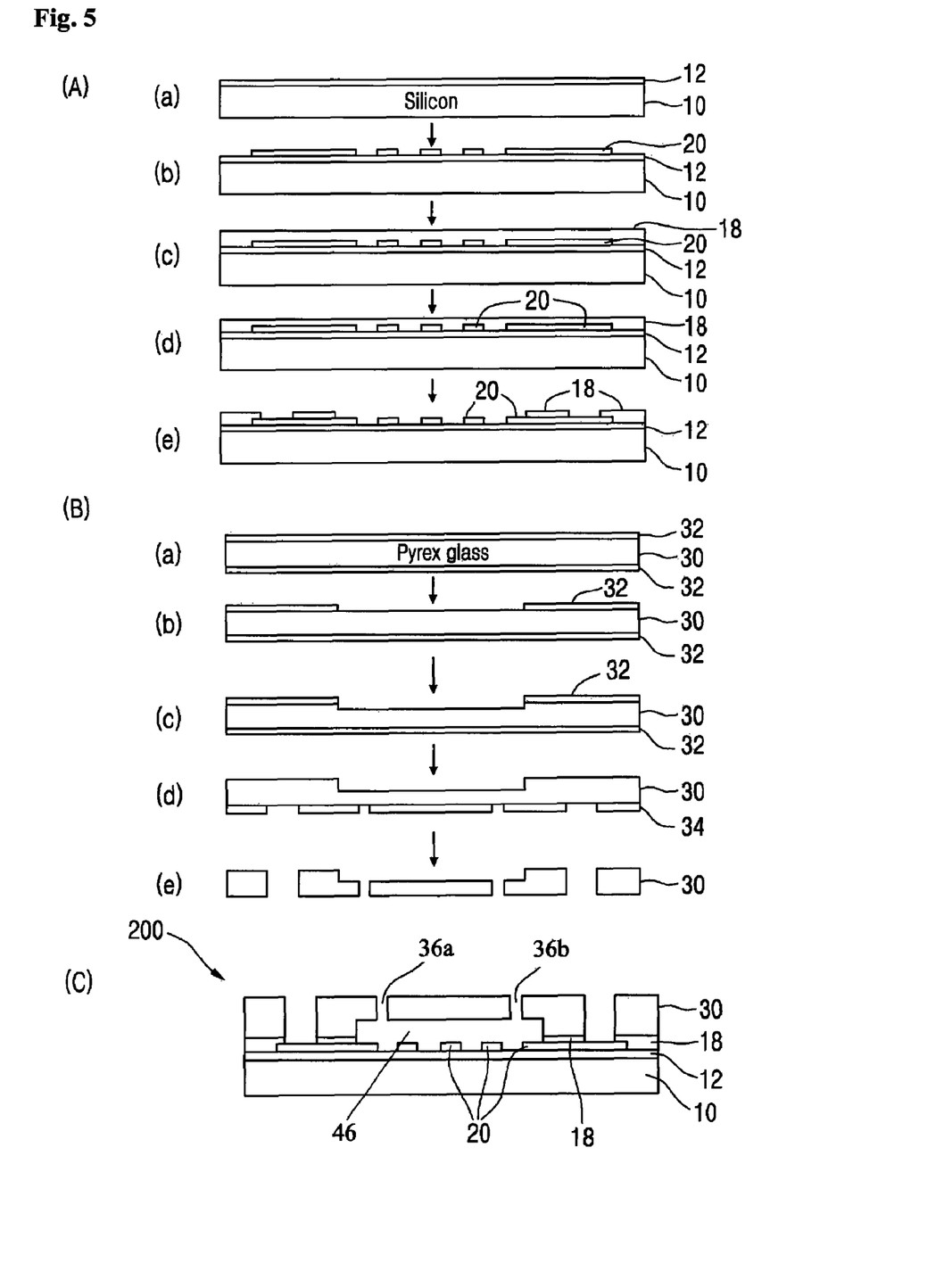
FIG. 5 is a flow chart of process that illustrates a method for preparing a PCR reaction chip used in the present invention.

Referring to FIG. 5, the process for manufacturing the PCR reaction chip (200) used in the present invention will be explained as below.

1. Formation of a Silicon Plate and Metal Electrodes

N-type silicon wafer (10) having 500 µm of thickness was thermally oxidized to make about 5,000 Å of a SiO$_2$ layer (12), an oxidized insulation layer (See the Step (a) of FIG. 5A). Ti/Au (300 Å/3000 Å) metal electrode (20) was patterned by using a conventional photolithography process, and a part of the electrode, which will be excluded from an IDE, was removed to form a fine IDE by dry-etching using ion milling (See the Step (b) of FIG. 5A). After that, a SiO$_2$ layer (18) of at least 1 µm of thickness was deposited onto the patterned metal electrode (20) by using chemical vapor deposition (CVD), vacuum evaporation or sputtering, etc. (See the Step (c) of FIG. 5A). Then, the SiO$_2$ layer (18) of the insulation layer was made even by using chemical mechanical polishing (CMP) (See the Step (d) of FIG. 5A). After that, the IDE was only treated with dry etching (RIE) or wet etching (BOE) to expose the surface of Au metal electrode. As a result, a portion of the insulation layer (18) binding to the glass plate (30) described below was formed (See the Step (e) of FIG. 5A).

The pattern of the metal electrode (20) is similar to that of the DNA hybridization chip (100) as shown in FIG. 3 (a), and a pair of electrodes (20a, 20b) is arrayed alternately in a predetermined interval with a finger-like shape.

Figure 7:
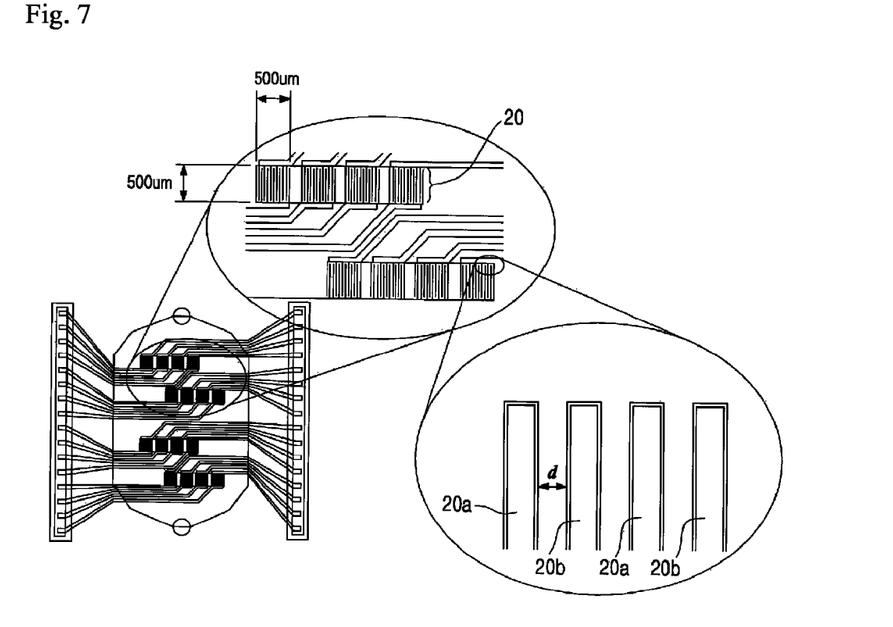
FIG. 7 depicts an electrode array type chip.

The electrode (20) has approximately 8.6 mm of diameter, but it is better to have as small diameter as possible in order to manufacture an electrode array type PCR reaction chip (See FIG. 7). The width (t) of each electrode (20a, 20b) is approximately 20 µm and the interval (d) between the electrodes is approximately 20 µm.

2. Preparation of a Glass Plate and Construction of a PCR Reaction Chip

As illustrated in FIG. 5B, Cr/Au (300 Å/3000 Å) metal film (32) was deposited on the upper and the lower surfaces of a conventional glass plate (Pyrex product) (30) used in a semiconductor process by using chemical vapor deposition (CVD), vacuum evaporation or sputtering, etc. (See the Step (a) of FIG. 5B). By using a general photolithography, a thin metal film (32) formed on the upper portion was patterned and wet-etched to form a protective layer (32) that is a part for protecting a glass plate portion processed later (See the Step (b) of FIG. 5B). Then, the other portion of the glass plate (30) that is not protected by the protective layer (32) was wet-etched to form a space of a reaction chamber in the PCR reaction chip (See the Step (c) of FIG. 5B). All the thin metal films formed on the upper and the lower surfaces were removed and the bottom surface of the glass plate was treated with a blue tape (any blue tape is available if suitable for patterning) patterning (34) in order to form an inlet/outlet (36a, 36b) of the PCR reaction chip (See the Step (d) of FIG. 5B). After that, penetration openings including inlet/outlet openings, etc. were made in the direction of thickness on the glass plate (30) by performing a sand blast process known in this field (See the Step (e) of FIG. 5B).

The silicon plate (10) previously manufactured on which the metal electrodes (20) are formed was bound with the glass plate (30) by using anodic bonding as illustrated in FIG. 5C. The resulting silicon plate (10) and glass plate (30) was diced to obtain a final PCR reaction chip (200).

The anodic bonding is a method for binding a silicon plate and a glass plate, in which cationic ions (for example, Na$^+$ ion) present within a glass plate are allowed to move to the opposite direction with respect to the position where the silicon plate and the glass plate are earthed, to form hydrogen bonds on the surfaces of the silicon plate and the glass plate and to bind the two plates by applying hot heat and high electric field.

In the PCR reaction chip (200) where the two plates are bound to each other, a plurality of metal sensing electrodes (20) are formed on the silicon plate (10) (See FIG. 5 and FIG. 6A), and primers (22) for a target DNA template are immobilized on the electrodes (See FIG. 6A). In addition, this silicon plate (10) is bound to the glass plate (30) in a predetermined distance to form a space for a reaction chamber (46) (See FIG. 5 and FIG. 6A).

The space of the reaction chamber (46) is a space where the impedance value is measured between the electrodes after being filled with a reference solution of deionized water. Also, the space of the reaction chamber (46) is a space that accommodates a target sample and a PCR reaction solution to conduct a PCR reaction, in which the target DNA template present in the target sample binds complementarily to the primers (22) immobilized on the metal electrodes (20) of the silicon plate (10) to proceed the PCR reaction.

Therefore, the change of the impedance value between the metal electrodes (20) according to PCR reaction will be detected to monitor whether the target DNA template is present within the target sample or not.

The glass plate (30) plays a role to protect the space of the reaction chamber (46) from outside environment. In addition, the glass plate (30) is perforated to have a fluid inlet (36a) in the direction of thickness and further perforated to have a fluid outlet (36b) in the direction of thickness on the opposite side of the fluid inlet (36a) (See FIG. 5 and FIG. 6A). As illustrated in FIG. 5 and FIG. 6A, the inlet (36a) and the space of the reaction chamber (46), and the outlet (36b) and the space of the reaction chamber (46) are communicated with each other to allow fluid to flow therethrough in the reaction chamber (46). Through the inlet (36a), the reference solution of deionized water, the PCR reaction solution and the target sample are introduced into the reaction chamber (46), and the reference solution of deionized water, the PCR reaction solution and the target sample are discharged from the reaction chamber (46) through the outlet (36b).

3. Construction of a Fluid Controlling Plate Based Upon PDMS

In order to control fluid flow within the PCR reaction chip (200), a fluid controlling plate (40) based upon PDMS is prepared and attached onto the glass plate (30) of the PCR reaction chip (200) manufactured previously.

The fluid controlling plate (40) of the PCR reaction chip (200) used in the present invention is preferable to be prepared with a transparent polymer in order to allow the inside of the chip (200) to be seen. Particularly, it is more preferable to be manufactured with PDMS (polydimethylsiloxane). Advantageously, PDMS is cheaper than silicone and easy to be manipulated, flexible and resistant to water when bound to another surfaces. Besides, PDMS does not cause any negative effect upon biomolecules due to its biocompatible property. However, it is preferably deposited with a reactive coating material or treated with graft copolymerization. Non-specific adsorption of hydrophobic components of cell such as protein may occur, if not coated. For example, when an injection opening (42), channels (44a, 44b) and a discharge opening (48) are coated with bovine serum albumin (BSA) in the fluid controlling plate (40), the non-specific adsorption of hydrophobic components can be minimized.

Above all, the fluid controlling plate (40) was designed by using a CAD (computer aided design) program. Then, the resulting design was printed on a photomask and impurities were removed. SU-8 of a negative type photoresist was spin-coated on the silicon wafer. A template for the fluid controlling plate (40) was manufactured by exposure and development using a photomask that has patterns of an injection opening (42), a valve structure (52), micro channels (44a, 44b) and a discharge opening (48). And then, PDMS of liquid phase was poured into the SU-8 template, solidified by heating and separated from the template. The resulting PDMS fluid controlling plate (40) was cut according to the size of the PCR reaction chip (200) and perforated at the position, where the injection opening (42) and the discharge opening (48), etc. were formed, in a desired size by using a punch. After that, the fluid controlling plate (40) as manufactured above was oxidized with plasma and then, attached to the corresponding position on the glass plate (30) of the PCR reaction chip (200).

FIG. 6A illustrates a longitudinal sectional view of the finally manufactured PCR reaction chip (200) to which the fluid controlling plate (40) is attached.

When the fluid controlling plate (40) is adhered onto the glass plate (30), an inlet micro channel (44a) that directs to introduce fluid into the inlet (36a), and an outlet micro channel (44b) that directs to discharge fluid from the outlet (36b) are formed. An injection opening (42) that introduces a reference solution of deionized water, a PCR reaction solution and a target sample is formed in the fluid controlling plate (40), by being penetrated into the fluid controlling plate. The injection opening (42) can introduce fluid into the reaction chamber (46) since it is communicated with the inlet micro channel (44a). In addition, a discharge opening (48) that discharges a reference solution of deionized water, a PCR reaction solution and a target sample is formed in the fluid controlling plate (40), by being penetrated into the fluid controlling plate. The discharge opening (48) can discharge fluid from the reaction chamber (46) since it is communicated with the outlet micro channel (44b).

Figure 6:
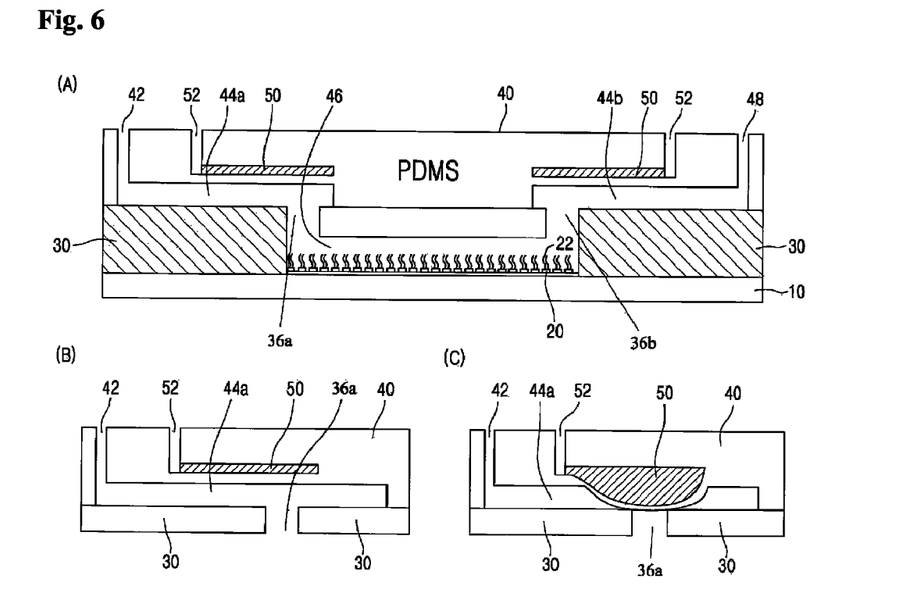
FIG. 6 is a sectional view that illustrates a PCR reaction chip to which a fluid controlling plate based upon PDMS is attached.

Furthermore, passages (52) extended longitudinally after being penetrated into the fluid controlling plate (40) in the direction of thickness, between the injection opening (42) and the reaction chamber (46), or between the discharge opening (48) and the reaction chamber (46) are formed in the fluid controlling plate (40) (See FIG. 6. (A) and (B)). The passage (52) plays a role of valve for the inlet micro channel (44a) and/or the outlet micro channel (44b). Silicone oil (50) is stored in the extended passage (52). As illustrated FIG. 6C, if nitrogen gas ($N_2$) is injected into the passage (52) in which the silicone oil (50) is stored, the oil (50) stored in the passage (52) expands and blocks the channels (44a, 44b) due to the oil expansion. Therefore, the fluid controlling plate (40) can block and control inflow of fluid from the injection opening (42) to the reaction chamber (46), and outflow of fluid from the reaction chamber (46) to the discharge opening (48).

Example 3-2

Immobilization of Oligonucleotide Primers on an Electrode

Above all, the electrode (20) of the PCR reaction chip (200) manufactured in Example 3-1 was washed for 30 minutes by using Piranha solution (mixture of $H_2SO_4$ and $H_2O_2$ in 70:30) to completely remove impurities on the electrode (20).

After that, one end (5' or 3') of the upstream primer and one end (5' or 3') of the downstream primer were immobilized on the electrode (20). Both the upstream primer and the downstream primer can be immobilized on the electrode (20), otherwise one end of any primer can be immobilized on the electrode and one end of the other primer can be mixed in a PCR reaction solution to perform a PCR reaction. For immobilization, 5'-SH—$(CH_2)_{24}$-GCC ATT CTC ACC GGA TTC AGT CGT C-3' of the upstream primer and 5'-SH—$(CH_2)_{24}$-AGC CGC CGT CCC GTC AAG TCA G-3' of the downstream primer, in which a thiol group is attached to a carbon chain (—$CH_2$—) at the 5' terminus of the primer oligonucleotide, is prepared and fixed on the surface of the metal electrode (20) by using a SAM (self-assembled method). In detail, 10 pmol/µl of SH-ssDNA upstream and/or downstream primers were reacted for 18 hours in TE buffer. As a result, the —SH group of the primer is reacted with the metal surface to immobilize the primer ssDNA (22) on the surface of the metal electrode (20). The immobilization process onto the metal surface performed in this example is substantially identical with that in example 1-2, as shown in FIG. 4.

Example 4

Analysis of PCR Reaction by Using a PCR Reaction Chip

The PCR reaction chip (200) on which primers are immobilized as manufactured in Example 3-2 (See FIG. 6) was used to examine whether a target DNA template is found within a target sample and a PCR reaction is performed or not.

Above all, deionized water of a reference solution having a high dielectric constant was introduced into the reaction chamber (46) of the PCR reaction chip (200) and then, the impedance value between the electrodes (20) was measured at room temperature by applying AC power. The applied magnitude of AC power was 100 mV and its frequency range was 1 to 32 MHz when the impedance value was measured.

After that, the reference solution was removed from the PCR reaction chip (200). Then, Promega PCR Core System II PCR Kit (PCR reaction solution commercially available in order to perform PCR easily; Promega Co. Ltd., USA) and DNA template were introduced into the reaction chamber (46) of the PCR reaction chip (200). The PCR reaction was repeated with 25 to 35 cycles as recommended by Promega, while adjusting time and temperature in the PCR reaction during each PCR cycle.

Again, the PCR reaction solution was completely removed from the PCR reaction chip (200) and deionized water was introduced into the reaction chamber. Then, the impedance value between the electrodes (20) was measured at room temperature by applying AC power. The applied magnitude of AC power was 100 mV and its frequency range was 1 to 32 MHz when the impedance value was measured.

Figure 9:
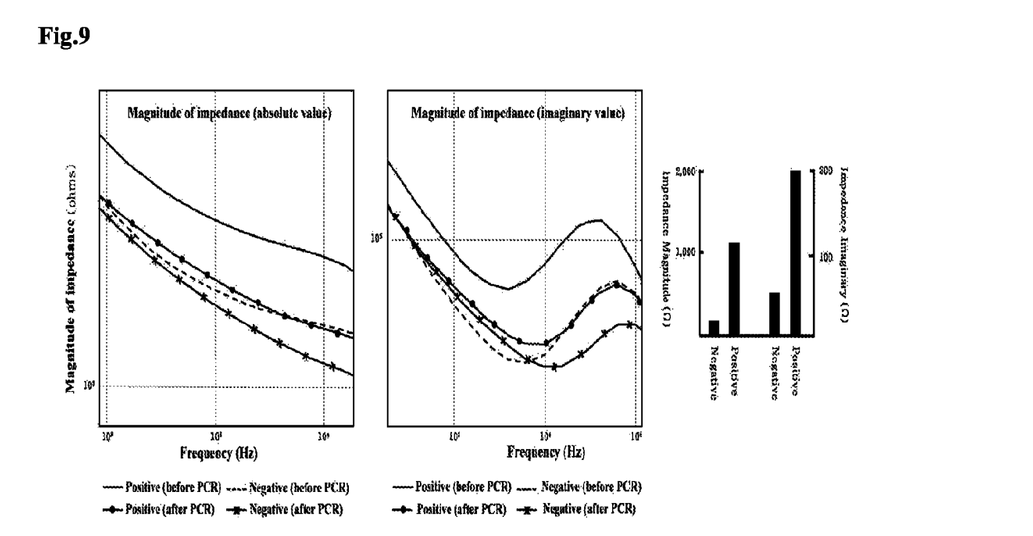
FIG. 9 depicts the change curve of the impedance value measured by using the method for detecting PCR reaction in the present invention.

As a result, the impedance value measured before and after the PCR reaction is illustrated in FIG. 9. In FIG. 9, contrasting to FIG. 1 in case of a conventional method, the impedance value measured before the PCR reaction and the impedance value measured after the PCR reaction were observed with two different curves, when this experiment is conducted by using a positive target sample containing the target DNA template. As illustrated in FIG. 9, it is confirmed that the impedance value should decrease when the target DNA template exists in the reaction solution during the PCR reaction. Therefore, it is confirmed that the impedance value will decrease as the conductance value increases due to the PCR reaction from ss-DNA to ds-DNA during the PCR reaction.

In the method of the present invention, the change of the capacitance value ($C_d$) after amplifying a target DNA template with PCR primers immobilized on a sensing electrode should reflect total change of the capacitance value ($C_T$) since it is not passed over by the capacitance value ($C_t$) of a buffer solution. Hence, the method of the present invention can permit electrical monitoring to detect the PCR reaction and the presence of the target DNA template, because two curves of the changes of the impedance value are observed before and after the PCR reaction, as shown in FIG. 9.

On the other hand, it is observed that the impedance value measured from a negative target sample without a target DNA template should be smaller than the impedance value of the positive case as shown in FIG. 9.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

The invention claimed is:

1. A method for detecting a biomolecule electrically comprising:
   (a) providing an apparatus for electrical detection comprising a reaction chamber receiving a target sample, and a plurality of sensing electrodes located in the reaction chamber for detecting a biomolecule within the target sample;
   (b) first introducing a reference fluid having a high dielectric constant into the reaction chamber provided in step (a), and then first measuring an impedance value or a capacitance value between the sensing electrodes;
   (c) removing the reference fluid having a high dielectric constant from the reaction chamber from step (b) and introducing a reaction solution and the target sample into the reaction chamber;
   (d) reacting the target sample under the reaction solution in the reaction chamber as prepared in step (c);
   (e) removing the reaction solution from the reaction chamber after step (d);
   (f) secondly introducing said reference fluid having a high dielectric constant again into the reaction chamber as provided in step (a), and then secondly measuring an impedance value or a capacitance value between the sensing electrodes; and
   (g) comparing the impedance value or the capacitance value measured in the step (b) with the impedance value or the capacitance value measured in the step (f).

2. The method as claimed in claim 1, wherein the impedance value or the capacitance value is measured according to frequency in the step (b) and the step (f), respectively by a measuring device using alternating current (AC) electric source.

3. The method as claimed in claim 2, wherein the impedance value or the capacitance value measured is illustrated as curves with respect to the frequency value, which determines the presence of the biomolecule or the reaction of the biomolecule on the sensing electrode in the target sample, in case that the curve of the impedance value or the capacitance value obtained in the step (b) is discriminated from the curve of the impedance value or the capacitance value obtained in the step (f).

4. The method as claimed in claim 1, wherein the reference fluid having a high dielectric constant has at least 4 of dielectric constant.

5. The method as claimed in claim 4, wherein the reference fluid having a high dielectric constant is distilled water or deionized water.

6. The method as claimed in claim 1, wherein the sensing electrodes are formed of interdigitated electrode.

7. The method as claimed in claim 6, wherein each interval between the sensing electrodes is 1 to 4 μm.

8. The method as claimed in claim 1, wherein the sensing electrode is bound with a receptor interacting with the biomolecule.

9. The method as claimed in claim 8, wherein the receptor is a probe or a primer.

* * * * *